(12) United States Patent
Hong et al.

(10) Patent No.: US 6,326,137 B1
(45) Date of Patent: Dec. 4, 2001

(54) HEPATITIS C VIRUS PROTEASE-DEPENDENT CHIMERIC PESTIVIRUS

(75) Inventors: Zhi Hong, Nanuet, NY (US); Vicki C. H. Lai, North Plainfield; Johnson Y. N. Lau, Warren, both of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/344,456

(22) Filed: Jun. 25, 1999

(51) Int. Cl.[7] ...................................................... C12Q 1/70

(52) U.S. Cl. ............................... 435/5; 435/23; 435/69.7; 435/70.1; 435/91.33; 435/235.1; 435/325; 536/23.4; 536/23.72

(58) Field of Search ............................... 536/23.4, 23.72, 536/23.2; 435/5, 23, 235.1, 325, 69.7, 70.1, 91.33

(56) References Cited

U.S. PATENT DOCUMENTS 6,242,187 6/2001 Capon et al. ............................ 435/6

FOREIGN PATENT DOCUMENTS

WO 98/00548 1/1998 (WO) .
WO 99/28482 6/1999 (WO) .

OTHER PUBLICATIONS

Frolov et al., cis–acting RNA elements required for replication of bovine viral diarrhea virus–hepatitis C virus 5' nontranslated region chimeras. RNA 4:418–1435, 1998.*

Cho et al., Construction of hepatitis C–SIN virus recombinants with replicative dependency on hepatitis C virus serine protease activity. Journal of Virological Methods 65:201–207, 1997.*

Bartenschlager et al. 1995, J. Virol. 67:3835–3844.

Butkiewicz et al., 1996, Virology 225: 328–338.

Filocamo, et al., 1997, J. Virol. 71:1417–1427.

Filocamo et al., 1999, J. Virology 73:561–575.

Kim et al., 1995, Biochem Biophys Res. Comm. 215:160–166.

Lin et al., 1995, J. Virol 69:4373–80.

Taremi et al., 1998, Protein Sci. 7:2143–2149.

Tratschin et al., 1998, J. Virol. 72:7681–7684.

Vassilev et al., 1997, J. Virol. 71:471–478.

* cited by examiner

*Primary Examiner*—Donna C. Wortman
(74) *Attorney, Agent, or Firm*—David B. Schram

(57) ABSTRACT

A chimeric bovine viral diarrhea virus (BVDV) that depends on a hepatitis C virus (HCV). The invention further relates to using the chimeric, infectious virus to screen for HCV NS3 inhibitor compounds in cell culture models or in animal models of viral infection.

20 Claims, 4 Drawing Sheets

VIRUS ASSEMBLY

+

| Npro | C | Erns | E1 | E2 | p7 | NS2 | NS3 | 4A | 4B | NS5A | NS5B |

BVDV NADL

| HCV NS3 | C | Erns | E1 | E2 | p7 | NS2 | NS3 | 4A | 4B | NS5A | NS5B |

BVDV/HCV NS3-wt

| HCV NS3 | C | Erns | E1 | E2 | p7 | NS2 | NS3 | 4A | 4B | NS5A | NS5B |

S139A

BVDV/HCV NS3-mt

HEPATITIS C VIRUS PROTEASE-DEPENDENT CHIMERIC PESTIVIRUS

FIELD OF THE INVENTION

The present invention relates to a chimeric pestivirus, such as bovine viral diarrhea virus (BVDV), that depends on a hepatitis C virus (HCV) protease function. The invention further relates to using the chimeric, infectious virus to screen for HCV NS3 inhibitor compounds in cell culture systems or in animal models of viral infection.

BACKGROUND OF THE INVENTION

Infection by hepatitis C virus (HCV) is a compelling human medical problem. HCV is recognized as the causative agent for most cases of non-A and non-B hepatitis, with an estimated prevalence of 170 million cases (i.e., 2–3%) globally [Choo, et al., Science, 244: 359–362 (1989); Kuo, et al., Science, 244: 362–364 (1989); Purcell, FEMS Microbiology Reviews, 14: 181–192 (1994); Van der Poel, C. L., Current Studies in Hematology and Blood Transfusion, H. W. Reesink, Ed., (Basel: Karger), pp. 137–163 (1994)]. Four million individuals may be infected in the United States alone [Alter, and Mast, Gastroenterol. Clin. North Am., 23: 437–455 (1994)].

Upon first exposure to HCV only about 10% or less of infected individuals develop acute clinical hepatitis, while others appear to resolve the infection spontaneously. In the most instances, however, the virus establishes a chronic infection that persists for decades [Iwarson, FEMS Microbiology Reviews, 14: 201–204 (1994)]. This usually results in recurrent and progressively worsening liver inflammation, which often leads to more severe disease states such as cirrhosis and hepatocellular carcinoma [Kew, FEM Microbiology Reviews, 14: 211–220 (1994); Saito, et al., Proc. Natl. Acad. Sci. USA 87:6547–6549 (1990)]. Currently, there are no broadly effective treatments for the debilitating progression of chronic HCV.

HCV is an enveloped positive-stranded RNA virus belonging to the Flaviviridae family. The HCV genome encodes a polyprotein of 3010–3033 amino acids [Choo, et al. Proc. Natl. Acad. Sci. USA, 88: 2451–2455 (1991); Kato, et al., Proc. Natl. Acad. Sci. USA, 87: 9524–9528 (1990); Takamizawa, et al., J. Virol., 65: 1105–113 (1991)]. The HCV nonstructural (NS) proteins provide catalytic machinery for viral replication. The NS proteins are derived by proteolytic cleavage of the polyprotein [Bartenschlager, et al., J. Virol., 67: 3835–3844 (1993); Grakoui, et al. J. Virol, 67: 2832–2843 (1993); Grakoui, et al., J. Virol., 67: 1385–1395 (1993); Tomei, et al., J. Virol., 67: 4017–4026 (1993)].

The order and nomenclature of the cleavage products are as follows: NH2-C-E1-E2-p7-NS2-NS4A-NS3-NS4B-NS5A-NS5B-COOH (FIG. 1) [Grakoui et al., 1993, J. Virol. 67:1385–95; Hijikata et al., 1991, PNAS 88:5547–51; Lin et al., 1994, J. Virol. 68:5063–73]. The three amino-terminal putative structural proteins, C (capsid), E1, and E2 (two envelope glycoproteins), are believed to be cleaved by a host signal peptidase of the endoplasmic reticulum (ER). The host enzyme is also responsible for generating the amino terminus of NS2. The proteolytic processing of the non-structural proteins are carried out by the viral proteases: NS2-3 and NS3, contained within the viral polyprotein. The NS2-3 protease catalyzes the cleavage between NS2 and NS3. It is a metalloprotease and requires both NS2 and the protease domain of NS3.

The NS3 protease catalyzes the rest of the cleavages in the nonstructural part of the polyprotein. The NS3 protein contains 631 amino acid residues and is comprised of two enzymatic activities: the protease domain contained within amino acid residues 1–181 and a helicase ATPase domain contained within the rest of the protein [Kim et al., 1995, Biochem Biophys Res. Comm., 215:160–166]. It is not known if the 70 kD NS3 protein is cleaved further in infected cells to separate the protease domain from the helicase domain, although no cleavage has been observed in cell culture expression studies.

The NS3 protease is a member of the serine protease family. Its active site consists of a His, Asp, Ser catalytic triad. Mutation of the Ser residue abolishes the ability to cleave at NS3/4A, NS4A/4B, NS4B/5A, and NS5A/5B junctions. The cleavage between NS3 and NS4A is intramolecular, whereas the cleavages at the NS 4A/4B, 4B/5A, 5A/5B sites may occur in trans.

Experiments using transient expression of various forms of HCV NS polyproteins in mammalian cells have established that the NS3 serine protease is necessary but not sufficient for efficient processing of all of these cleavages. HCV NS3 protease requires a cofactor to catalyze some of these cleavage reactions. Efficient proteolytic processing at NS3/4A, NS4A/4B, NS4B/5A, and NS5A/5B sites within the non-structural domain of hepatitis C virus requires a heterodimeric complex of the NS3 serine protease and the NS4A protein. [Bartenschlager et al. 1995, J. Virol. 67:3835–3844; Failla et al., 1994, J. Virol. 68:3753–3760]. A 13-amino acid synthetic NS4A peptide, corresponding to the central hydrophobic domain of NS4A protein, spanning residues 21–33 has been shown to be sufficient for activation of NS3 protease [Butkiewicz et al., 1996, Virology, 225: 328–338]. A smaller domain (amino acid residues 22–30) of NS4A has been shown to be sufficient for activation of the protease [Lin et al., 1995, J. Virol 69:4377–80].

The recently published three dimensional structure of the NS3 protease [im et al, 1996, Cell 87:343–355; Yan et al, 1998, Protein Sci. 7:837–847] revealed that the N-terminal 37 residues of NS3 adopt a β (residues 6–9)-α (residues 14–22)-β (residues 33–37) structure upon binding of a synthetic peptide corresponding to the central hydrophobic domain spanning residues 21–32 of NS4A protein.

The Flaviviridae family comprises two other genera of single-stranded positive-sense RNA viruses: flaviviruses and pestiviruses [Rice, In *Virology, Third Ed,* B. N. Fields, D. M. Knipe, and P. M. Howley (ed.), Raven Press: New York (1996)]. Bovine viral diarrhea virus (BVDV) is a prototype virus in the Pestivirus genus. Its RNA genome is one of the largest (12.5 kb) among members of the Flaviviridae family [Collett, et al., Virol. 165:191–199 (1988)]. As one of the most characterized members of the Flaviviridae family, BVDV provides a good model system for HCV. Similar to HCV, it consists of (1) a long 5' untranslated region (UTR), which contains an internal ribosomal entry site (IRES) for translation of viral proteins [Poole, et al., Virol. 206:750–754 (1995); Frolov, et al., RNA 4:1418–1435 (1998); Chon, et al., Virol. 251:370–381 (1998)]; and (2) a single large open reading frame (ORF) which encodes a polyprotein of approximately 3,900 amino acids [Meyers and Thiel., Adv. Virus Res. 47:53–118 (1996); Collett, supra; Rice, supra]. Unique to pestiviruses, the first virally encoded protein is Npro, a cysteine protease, only responsible for the cleavage between Npro and the capsid protein (C) [Stark, et al., J. Viro. 67:7088–7095 (1993); Rumenapf, et al., J. Virol. 72:2544–2547 (1998)]. Interestingly, Npro is not essential for viral growth and its coding region can be replaced by a ubiquitin gene directly fused in-frame to the capsid gene. The resulting chimeric virus has growth properties similar to the wild type viruses [Tratschin, et al., J. Virol. 72:7681–7684 (1998)]. Several other investigators have also demonstrated that Npro is not required for pestiviral replication [Mittelholzer, et al., Virus Res. 51:125–137 (1997); Behrens, et al., J. Virol. 72:2364–2372 (1998)].

Current therapies with alpha interferon alone and the combination of alpha interferon-ribavirin have been shown to be effective in a portion of patients with chronic HCV infection [Marcellin et al., Ann. Intern. Med. 127:875–881 (1997); Reichard et al., Lancet 351:83–87 (1998)]. Vaccine development has been hampered by the high degree of immune evasion and the lack of protection against reinfection, even with the same inoculum [Farci et al., Science 258: 135–140 (1992); Kao et al., J. Med. Virol. 50:303–308 (1996); Shimizu et al., J. Virol. 68:1494–1500 (1994); Wyatt et al., J. Virol. 72:1725–1730 (1998)]. Development of small molecule inhibitors directed against specific viral targets has thus become the focus of anti-HCV research. The determination of crystal structures for NS3 protease [Kim et al., Cell 87:343–355 (1996); Love et al., Cell 87:331–342 (1996); Yan et al., Protein Sci. 7:837–847 (1998)] and NS3 RNA helicase [Yao et al., Nat. Struct. Biol. 4:463–467 (1997)] has provided important structural insights for rational design of specific inhibitors. It is believed that inhibitors of protease function will inactivate the virus.

The lack of broadly effective treatments for the debilitating progression of HCV has prompted an intensive effort among various pharmaceutical companies to develop an effective and small molecule inhibitor against HCV infection. Many high throughput enzyme-based screening assays have been developed, which are likely to yield potential inhibitors targeting at HCV NS3 serine protease/RNA helicase. Further development of these inhibitors have to rely on a cell-based assay system to demonstrate their antiviral efficacy. However, the lack of a convenient and reliable cell-based assay that supports HCV replication or mimics HCV enzymatic functions poses an obstacle for inhibitor development. The currently available chimpanzee models of HCV infectivity are simply too expensive to be practical for early stage evaluation of potential inhibitors.

Because the HCV NS3 protease cleaves non-structural HCV proteins necessary for HCV replication, the NS3 protein can be a target for the development of therapeutic agents against the HCV virus. Various U.S. Patents disclose HCV protease, including U.S. Pat. No. 5,371,017 (isolated polynucleotide which encodes only the HCV protease or an active HCV protease analog), and U.S. Pat. Nos. 5,585,258 and 5,712,145 (compositions comprising a Hepatitis C Virus NS3 domain protease or truncation analog).

In an effort to create a system for analysis of NS3 protease activity in cultured cells, Filocamo, et al. [J. Virol. 71:1417–1427 (1997)] constructed a family of chimeric Sindbis viruses carrying sequences coding for active HCV NS3 and an NS3 cleavage site. However, recombination events spliced the HCV gene out of the chimeric Sindbis genome. To overcome this problem and force retention of HCV sequences, a second NS3 cleavage site was required to be introduced into the genome, so that deletion of the HCV protease sequences would inactivate the virus. The resulting virus, while infectious, replicated at a much lower rate than wild-type, and displayed a temperature dependence in the formation of plaques. This chimeric virus construct has been used to select functional HCV NS3-NS4A protease variants [Filocamo et al., J. Virology 73:561–575 (1999)]. It has not, however, been shown to be useful for testing potential NS3 inhibitors in cell culture systems or in animal models.

Thus, there is a need in the art to develop an infectious viral model to test the activity of candidate HCV NS3 inhibitor compounds in cell culture and animal models of viral infection. The present invention addresses this and other needs in the art.

SUMMARY OF THE INVENTION

The invention advantageously provides a chimeric pestivirus, in which a proteolytic function responsible for cleaving the junction between viral polyproteins is replaced by that of HCV NS3 protease. However, the chimeric virus remains functional and infectious.

Figure 2:
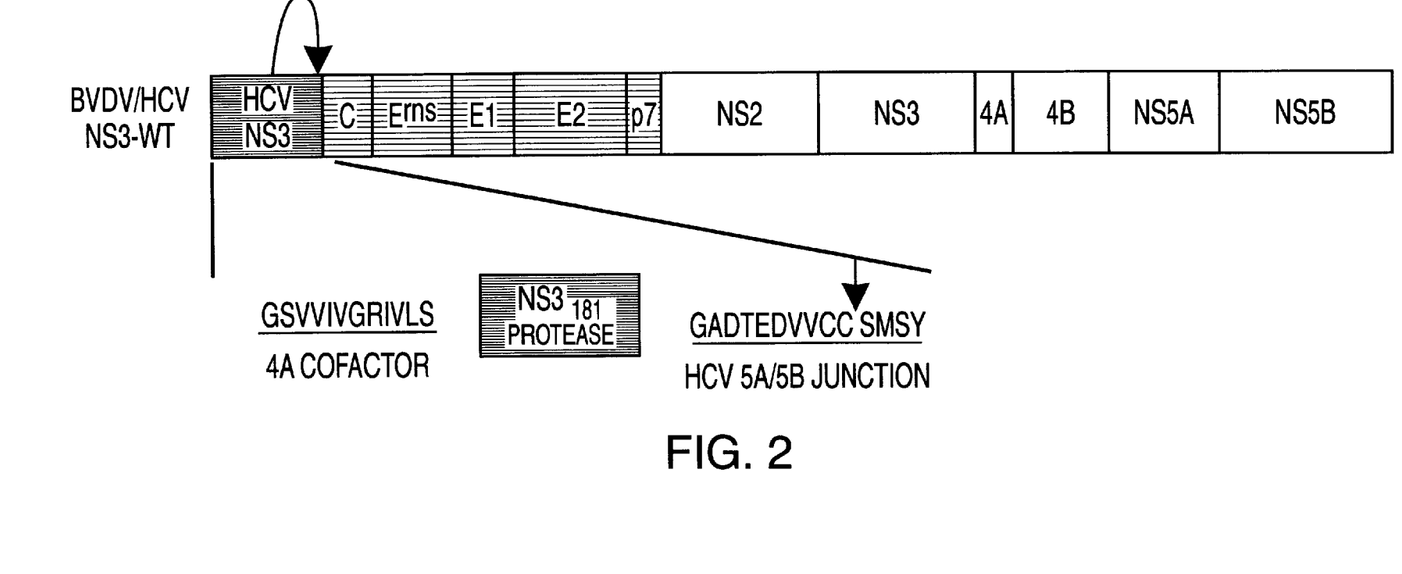

In a first aspect, the present invention provides a nucleic acid construct encoding a chimeric Hepatitis C Virus (HCV)-pestivirus genome. The nucleic acid construct comprises a pestivirus genome wherein (i) a pestivirus protease gene, or a non-essential pestivirus gene, is replaced with a gene encoding a functional HCV protease, and (ii) each junction site recognized by the pestivirus protease is replaced with a junction site recognized by an HCV protease. In a specific embodiment, the genome has a structure as shown in FIG. 2. In a more specific embodiment, the genome has a sequence as depicted in SEQ ID NO:1.

In conjunction with the recombinant nucleic acids described above, the invention further provides an infectious, plaque-forming chimeric HCV pestivirus. The virus has a genome comprising a pestivirus genome wherein (i) a pestivirus protease gene, or a non-essential gene, is replaced with a gene encoding a functional HCV protease, and (ii) each junction site recognized by the pestivirus protease is replaced with a junction site recognized by the HCV protease.

Also provided is a method for propagating an infectious, plaque-forming chimeric HCV-pestivirus, which method comprises culturing a cell containing the chimeric pestivirus genome under conditions that permit production of viable virus. Such a method can be further adapted for screening for a compound that inhibits an HCV protease, which method comprises evaluating viral infection of the cells cultured under conditions that permit production of viable viruses, wherein one set of cells are cultured in the presence of a candidate compound (test cells) and a different set of cells are cultured in the absence of the candidate compound (control cells), and wherein a reduction in viral infection in test relative to control cells indicates that the compound inhibits an HCV protease.

The viruses of the invention have practical application in a method of screening for a compound that inhibits HCV in vivo by inhibiting an HCV protease. This method comprises evaluating viral load or disease progression, such as pathogenesis, or both in susceptible animals infected with the virus of the invention when treated (test animal) or untreated (control animal) with a candidate compound, wherein a reduction in viral load or disease progression in a test animal relative to a control animal indicates that the compound inhibits HCV protease function in vivo.

It is an object of the invention to provide a chimeric virus that can be propagated in vitro (in a cell culture) or in vivo (in an animal model), in which viral infectivity requires a functional HCV NS3 protein.

Thus, it is a further object of the invention to provide an in vitro cell culture system and an in vivo animal model for evaluating inhibitors of HCV NS3 protease.

The present invention meets these and other objects of the invention, as set forth in greater detail in the Detailed Description and Examples, including the accompanying Drawings.

BRIEF DESCRIPTION OF THE DRAWINGS

FIG. 2. Schematic construct of the functional HCV NS3-BVDV. The functional HCV NS3, including the tethered NS4A cofactor sequence (SEQ ID NO:2) and the HCV NS5A/5B junction sequence (SEQ ID NO:3) (which provides a HCV NS3 substrate sequence between the HCV NS3 and BVDV core proteins) are shown.

DETAILED DESCRIPTION OF THE INVENTION

The present invention advantageously provides a class of chimeric flaviviridae that depend on HCV protease activity for function. Such chimeric viruses can advantageously be used in cell cultures or in vivo non-human animal models for viral activity. The invention is based, in part, on construction of a chimeric BVDV, in which HCV NS3 is substituted for BVDV Npro. The coding region of Npro was replaced by a gene coding for the NS4A cofactor-tethered HCV NS3 protease domain. This tethered HCV NS3 catalytic domain was then linked in-frame to the capsid (C) of BVDV through an HCV NS5A/5B junction site. In the resulting chimeric BVDV (SEQ ID NO:1), the proteolytic function of BVDV Npro, which is responsible for cleaving the junction between Npro and C was now replaced by that of HCV NS3 protease. The active NS4A-tethered HCV NS3 protease (NS3-wt) cleaves the NS5A/NS5B junction, releasing the BVDV capsid from fusion with the HCV NS3 protease domain. As a control, a chimeric construct with an inactive tethered HCV NS3 NS3-mt, with a mutation at amino acid 139 from Serine to Alanine) was also constructed. The lack of HCV NS3 protease activity in this control results in non-cleavable HCV NS3-BVDV capsid fusion protein, thus rendering the capsid non-functional for encapsidation of viral genome.

Figure 1A:
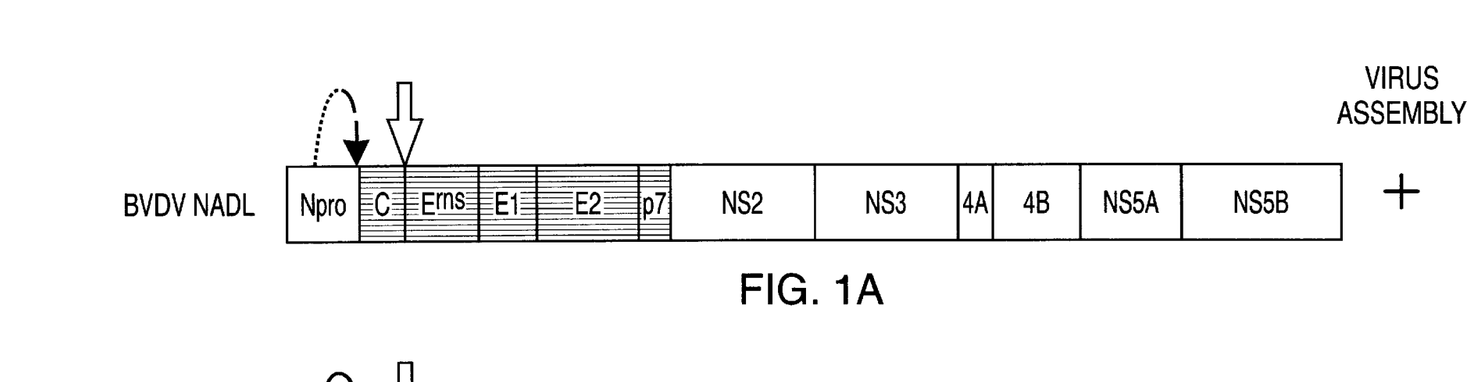
FIGS. 1A, 1B, and 1C. Schematic drawings of (A) the BVDV genome, (B) a chimeric BVDV genome in which a functional HCV NS3 comprising an HCV NS4A cofactor sequence is substituted for BVDV Npro (SEQ ID NO:1), and (C) a chimeric BVDV genome in which a non-functional (Ser139→Ala) HCV NS3 is substituted for BVDV Npro. Constructs (A) and (B) produce functional virus; construct (C) does not.
Figure 1B:
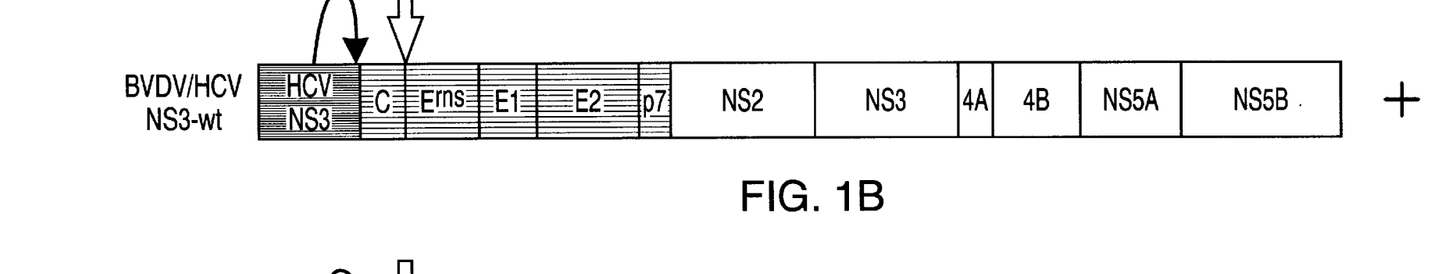
Figure 1C:
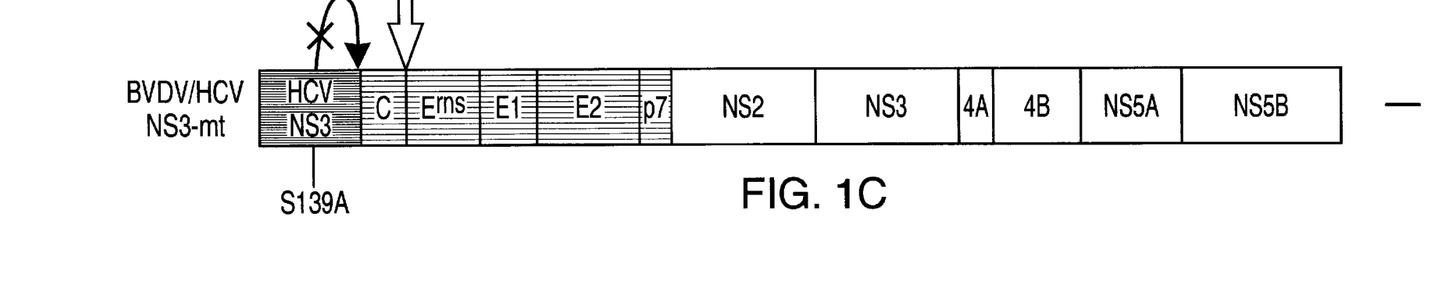

To demonstrate HCV NS3 dependence of the chimeric virus, two chimeric clones, BVDV/HCV NS3-wt (containing a function HCV NS3) and BVDV/HCV NS3-mt (containing a, mutated, non-functional HCV NS3), were constructed as illustrated in FIGS. 1B and 1C. The full-length RNA transcripts were transfected into MDBK cells. The RNA transcript from the chimeric BVDV/HCV NS3-wt clone generated cytopathic viruses, whereas the mutant clone (BVDV/HCV NS3-mt) failed to produced any signs of infection. Further evidence of functionality of the chimeric viruses was obtained by reverse transcription and polymerase chain reaction (RT-PCR) of plaque-purified virus, which yielded a predicted HCV NS3-BVDV C fragment, suggesting that the viruses in the supernatant are the chimeric BVDV (no contaminating DNA was detected). Cloning and sequencing of the fusion fragment further confirmed the identity of its origin from the chimeric clone. Western analysis demonstrated that plaque-purified viruses produced HCV NS3 protease in the cells corresponding to the size of the NS4A-tethered HCV protease domain. The cytopathic effect of the chimeric virus correlates with the production of both BVDV NS2-3 and NS3 proteins.

The invention of this HCV NS3-dependent BVDV, and related chimeric pestiviruses will allow evaluation of the efficacy of protease inhibitors derived from in vitro enzyme-based screens in a cell-based antiviral assay. This will impact the development of NS3 protease-specific inhibitors against HCV.

The term "chimeric" is used herein in its usual sense: a construct resulting from the combination of genes from two different sources, in which the different parts of the chimera function together. The genes are fused, where necessary in-frame, in a single genetic construct. As used herein, the term "chimeric" refers specifically to a pestivirus genome in which a functional HCV NS3 is inserted, and the genome is further modified to require activity of the HCV NS3 for infectivity. This latter modification comprises substituting a native protease recognition site with an HCV NS3 recognition site, so that expression of functional viral proteins and thus viral infectivity depends on HCV NS3 activity.

As used herein, the terms "HCV NS3" and "HCV protease" are used interchangeably, to refer to the HCV proteolytic protein. Unless otherwise indicated, both terms are intended to refer to a functional, i.e., proteolytically active, form of the protein. For example, a functional HCV NS3/protease can be a full length NS3 protein. Alternatively, it can be a truncated protein, comprising the proteolytic domain. Preferably, a functional protease includes the NS4A cofactor, which can be tethered to the protease in a fusion construct.

The term "junction site" is used herein to refer to the amino acid sequence joining two different proteins of a viral polyprotein that is recognized and cleaved by a protease, e.g., HCV NS3. Various HCV NS3 junction sites are known, including the NS3/NS4A, NS4A/NS4B, NS4B/NS5A, and NS5A/NS5B junction sites. Any of these can be used to substitute for an endogenous junction site of the virus used in the chimeric construct. In a specific embodiment, an HCV NS5A/NS5B junction is used.

The term "genome" as used herein refers to the genome of the pestivirus that is modified by insertion or substitution of HCV NS3 sequences and HCV NS3 junction sequences. In some instances, the virus may be referred to as a parent virus, or the genome of the virus as the backbone. In general, the chimeric virus will consist mostly of the parent virus genome. Thus, many of the features of the parent virus will be preserved in the chimeric virus, including infectivity, tropism, life cycle, and other characteristics.

The term "pestivirus" is used herein to refer to a genus in the Flaviviridae family that typically infect pigs and ruminents. Specific examples include classic swine fever virus (CSFV), sheep border disease virus (BDV), and bovine viral diarrhea virus (BVDV) [see Thiel et al., Fields Virology, Third Edition, edited by B. N. Fields et al., Chapter 33, pp. 1059–1073 (1996); see also Monath and Heinz, ibid., Chapter 31, pp. 961–1034 (flaviviruses)]. The advantage of these viruses includes (1) tropism for animals, which makes them safer and provides animal models of infectivity; (2) the presence of Npro; and (3) knowledge of and simplicity of the genome. Equivalent flaviviruses can be used instead of BVDV or another pestivirus.

As used herein, "infectious" refers to the ability of a virus to replicate in a cell and produce viral particles. In one embodiment, plaque formation of cells in cell cultures evidence that a viral construct is infectious. Plaque formation is also termed "cytopathic effect" or "cell lysis". The analogous effect in vivo is development of either an acute or chronic viral infection, which may include either overt pathology or merely replication and propagation of the virus in an infected animal. In another embodiment, detection of expressed proteins form the chimeric viral genome indicates that the viral construct is infectious.

The term "viral load" is used herein to refer to a quantitative amount of virus in an animal. Such an animal can be referred to as "viremic". "Disease progression" refers to the course of disease or symptoms of an infected animal, and may include acute or chronic disease symptoms. "Pathothogenesis" is a particular indication of disease progression, and refers to the pathogenic effects of viral infection, including morbidity and mortality.

A "construct" is a chimeric virus or nucleic acid encoding a chimeric virus, such as positive viral genomic RNA or a DNA that can be transcribed to produce viral genomic RNA.

Various aspects of the invention are disclosed in greater detail in the following sections related to NS3, strategies for preparing chimeric viruses, and screening assays with such viruses. The headings (bold), subheadings (bold, italics), and sections of the application are provided to two different plaque-purified viruses facilitate understanding of the invention, and are not intended to be limiting.

Molecular Biological Techniques

In accordance with the present invention there may be employed conventional molecular biology, microbiology, and recombinant DNA techniques within the skill of the art for the production of NS5B. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, New York (herein "Sambrook et al., 1989"); DNA Cloning: A Practical Approach, Volumes I and II (D. N. Glover ed. 1985); Oligonucleotide Synthesis [M. J. Gait ed. (1984)]; Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; A Practical Guide To Molecular Cloning [B. Perbal (1 984)]; Current Protocols in Molecular Biology, John Wiley & Sons, Inc. [F. M. Ausubel et al. (eds.) (1994)].

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. In discussing the structure of particular nucleic acid molecules, sequences or regions may be described herein according to the normal convention of giving only the sequence in the 5' to 3' direction. A "recombinant DNA molecule" is a DNA molecule that has undergone a molecular biological manipulation.

The term "host cell" means any cell of any organism that is capable of infection by or propagation of a chimeric virus construct of the invention. Host cells can further be used for screening or other assays, as described infra.

A "coding sequence" or a sequence "encoding" an expression product such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. In the present invention, translation initially yields a polyprotein, which is cleaved during post-translational processing, particularly by a functional HCV NS3 protease, to yield functional viral proteins.

The term "gene" means a DNA sequence that codes for or corresponds to a particular sequence of amino acids which comprise all or part of one or more proteins or enzymes.

A coding sequence is "under the control" or "operatively associated with" transcriptional and translational control sequences in a cell when RNA polymerase transcribes the coding sequence into mRNA, which is then translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a mRNA or a protein. The expression product itself, e.g. the resulting protein, may also be said to be "expressed" by the cell.

The term "transfection" means the introduction of a foreign nucleic acid into a cell. The introduced gene or sequence may also be called a "cloned" or "foreign" gene or sequence, may include regulatory or control sequences, such as start, stop, promoter, signal, secretion, or other sequences used by a cell's genetic machinery. A host cell that receives and expresses introduced DNA or RNA has been "transformed" and is a "transformant".

In a specific embodiment, the term "about" or "approximately" means within a statistically meaningfiul range of a value. Such a range can be within an order of magnitude, preferably within 50%, more preferably within 20%, more preferably still within 10%, and even more preferably within 5% of a given value or range. The allowable variation encompassed by the term about or approximately depends on the particular system under study, and can be readily appreciated by one of ordinary skill in the art.

HCV NS3 Constucts

Either full length or truncated HCV NS3 can be employed, as can variants of the polypeptide. Examples of functional NS3 proteins are described, inter alia, in U.S. Pat. No. 5,371,017 and its progeny. In a preferred embodiment, the functional NS3 protein is a tethered NS3-NS4A construct, e.g., as described in U.S. patent application Ser.

No. 09/198,723 filed Nov. 24, 1998 and International Patent Application PCT/US98/24528 filed Nov. 24, 1998, which are each specifically incorporated herein by reference in their entireties. The foregoing patent applications disclose NS4 tethered to full length NS3, as well as to the NS3 catalytic domain, and functional point mutants. In a specific embodiment, exemplified in this application, a tethered NS3-NS4A construct as described in Taremi et al. [Protein Sci. 7:2143–2149 (1998)], which is specifically incorporated herein by reference in its entirety, is used.

Variants of HCV NS3 are polypeptides that have proteolytic activity specific for junction sites recognized by NS3, but may have a divergent sequences, either at the nucleotide or amino acid level. For example, "sequence-conservative variants" of NS3 are those in which a change of one or more nucleotides in a given codon position results in no alteration in the amino acid encoded at that position. "Function-conservative variants" of NS3 are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like).

Construction of Chimeric Viruses

Selection of the parent virus for construction of a chimeric genome will depend on a number of criteria. One is the availability of an infectious clone of the virus. Preferably a member of the Flavivinidae family that is not infectious in humans is selected, so that all work can be performed with no issues of biohazards. In a preferred embodiment, the parent virus is a pestivirus; in a specific embodiment, it is BVDV. BVDV has a number of surprising advantages, including the ability to delete the Npro coding region without affecting infectivity, the availability of an infectious clone, the availability of cell lines that can propagate the virus in vitro, and the ability to infect animals with the virus. In an alternative preferred embodiment, a virus that is infectious in mice, rats, or other small animals is used, since these animals provide a convenient and well studied model for screening (see below).

There are two preferred target sites in any of pestivirus that can be used to construct a chimeric virus of the invention for insertion or substitution of the HCV protease: a non-essential protein, which could itself have proteolytic activity, and a wildtype protease found in the viral genome of the Flaviviridae. Such proteins are described for many viruses. In particular, all viruses in the Flaviviridae family encode an NS3 protein.

In a preferred embodiment, the native or wildtype viral protein is a non-essential protease, such as the BVDV Npro.

The actual molecular biological techniques required to substitute HCV protease coding sequences and junction coding sequences are routine. For example, PCR can be employed to prepare the fusion polypeptide comprising an NS4A tethered NS3 protease joined to a pestivirus core protein. PCR amplification also permits construction of the full length recombinant chimeric virus.

Screening

The chimeric constructs are primarily useful as secondary validation assays for compounds selected in primary screens for the ability to inhibit HCV protease. These secondary screens can be divided into in vitro cell culture assays, and in vivo animal models of viral infection and, optimally, pathogenicity. The selection of cells and animals for these assays will depend on the tropism of the virus which is used as the backbone for substitution with the HCV NS3. Viral tropism of the parent virus will determine the appropriate host cells and animal models for these assays.

Originally pestiviruses were isolated from the species in which they induced disease, but these viruses are able to cross species barriers. Pigs can become viremic with pestiviruses originating from ruminants without developing clinical disease. CSFV may be transmitted to sheep, goats, and cattle [Thiel et al., supra]. Pestiviruses can be propagated in cultures of primary and permanent cells of their respective host species, and are capable of adaptation to a variety of heterologous cell types (with the apparent exception of cultured human and rodent cells).

Any discovery process can be used to evaluate the compounds for use in secondary screens of the invention. As described in PCT/US98/24528, one can use the covalent NS4A-NS3 complexes, along with known synthetic substrates, to develop high throughput assays. These can be used to screen for compounds that inhibit proteolytic activity of the protease. This is carried out by developing techniques for determining whether or not a compound will inhibit the covalent NS4A-NS3 complexes of the invention from cleaving the viral substrates. If the substrates are not cleaved, the virus cannot replicate. One example of such a high throughput assay is the scintillation proximity assay (SPA). SPA technology involves the use of beads coated with scintillant. Bound to the beads are acceptor molecules such as antibodies, receptors or enzyme substrates which interact with ligands or enzymes in a reversible manner. U.S. Pat. No. 5,597,691 also describes assays for identifying HCV NS3 inhibitors.

Cell culture assays. These assays can be performed by transfecting cultured cells with transcribed viral genomic RNA encoding the chimeric virus. In a specific example, MDBK cells are used, particularly as these cells are infected by BVDV.

To perform these assays, cultured cells are infected with the chimeric viral construct. Some infected cells are treated with the test compound. Negative control cells are untreated or treated with a sham test compound (buffer or buffer with compound not known to inhibit NS3 activity). Other positive control cells may be treated with a compound known to inhibit HCV NS3 activity. The cells are maintained in culture under conditions that permit plaque formation or development of the cytopathic effect (CPE). The test and control cultures are then evaluated for inhibition of the chimeric virus. If cells treated with a test compound nevertheless develop plaques or CPE, the compound does not effectively inhibit NS3 activity. However, if cells treated with a test compound do not form plaques or develop CPE (and the negative controls do), then the compound is effective at inhibiting HCV NS3.

In vivo animal models. The secondary assays described above can be used to evaluate activity of a test compound in vivo, using animals susceptible to infection with the chimeric virus (based on the tropism of the parent virus). These animals can be treated with the test compound (control animals would not be treated, and, if available, a positive control could also be employed). A compound that protects animals from infection by the chimeric virus, and particularly from pathogenicity of the infectious virus, would be an attractive candidate for development of an agent for treatment of HCV. Moreover, the animal models provide a platform for pharmacokinetic and toxicology studies.

Infectivity can be evaluated either by detecting virus, i.e., viral load, or by observing disease progression in the animal. Virus (viral load) can be detected by the presence of viral nucleic acids, e.g., detected by PCR or RT-PCR or direct hybridization techniques. It can also be detected, if present in sufficient amount, by the presence of viral proteins, e.g., detected by immunoassay or biochemical techniques. In another alternative, extracts from tissue samples from the animal are used to infect cells in culture; the presence of virus is detected by development of CPE. Pathogenicity is evaluated by gross examination of symptomology of the animal, such as fever, fatigue, discoordination, convulsions, and other neurological symptoms, diarrhea, hemorrhage, mortality, etc. [see, Thiel et al., supra]. Either evaluation can be part of an acute condition, i.e., arising and resolving over a short period, or a chronic condition, i.e., persisting for a long period of time.

In a specific embodiment, seronegative and specific-pathogen-free (SPF) weaned calves, four months of age, are selected from a SPF herd for challenge by a chimeric BVDV. Each BVDV (chimeric or cytopathic wild-type) ($10^7$ $TCID_{50}$) is inoculated into one calf by aerosol-instillation of 3 ml of tissue culture fluid into the nostrils. One sham-inoculated (mock infection) calf is included and housed separately. The sham-inoculated control calf is administered with the same volume of tissue culture supernatant as used in the test.

All calves are subjected to a daily clinical monitoring throughout the experiment (approximately 15 days). Records of rectal temperature and objective indicators of clinical signs of disease are maintained. Indicators of respiratory and digestive tract function are monitored very closely and recorded. Blood is collected daily from the jugular vein of each calf into sterile EDTA-containing Vacutainer tubes. These samples are used for determination of total and differential white blood cells (WBC) and platelets in a Coulter instrument and to perform virus isolation procedures. A smear is prepared for differential peripheral leukocyte determinations following cytological staining. Nasal swabs are collected daily into a 4 ml vial containing refrigerated cell culture medium and antibiotics. Fecal samples are collected from the rectum daily. Nasal swabs, fecal samples, and EDTA-preserved peripheral blood samples are kept refrigerated until processed for virus isolation and quantitation in the laboratory (within 24 hours of collection). The experiment is terminated at 15 days after inoculation, when the immune response is expected to have completed virus clearance. The severity and consequences of BVDV infection is not only reflected in the clinical responses, but is also impacted by the hematological and virological parameters. It is anticipated that the cytopathic wild-type BVDV as well as the more virulent chimeric BVDV cause lymphopenia and thrombocytopenia in calves. In contrast, less virulent mutants result in minor changes in the clinical outcomes.

The presence of BVDV and its concentration in the three clinical samples collected is determined prior to freezing. Virus infectivity of clinical samples is analyzed by a plaque assay (for cytopathic BVDV) of the samples in primary fetal bovine lung cells. Plaques are developed by removing the agar and fixing the monolayers with methanol-crystal violet for cytopathic BVDV. The plaque counts reveal if BVDV is present and its titer. In addition, an estimate of the plaque morphology heterogeneity of the recovered virus is obtained.

First, EDTA-preserved blood samples are separated by centrifugation into plasma and cell fractions. The plasma is aspirated and 5 serial 10-fold dilutions are prepared in Dulbecco-buffered saline solution containing sodium citrate. Each dilution (2 ml) is inoculated onto each well of sub-confluent fetal bovine lung cells in a 6-well cluster tissue culture plate. After adsorption for 1 hour incubating at 37° C., the inoculum is removed and the cells are overlayed with medium containing 1% agarose. The mononuclear cells (MNC) are purified from the cell pellet containing the red blood cells by ficoll-hypaque density centrifugation. The cells are counted with a hemocytometer and resuspended at $10^6$ per ml. Five serial ten-fold dilutions of the MNC are prepared in cell culture medium and 1 ml of each are inoculated onto each well of a 6-well cluster plate as described above for the plasma.

Second, fecal samples are weighed and diluted with ice-cold cell culture medium containing antibiotic and antimycotic to yield a 10% weight/volume suspension. The samples are vortexed briefly and then centrifuged at 10,000×g for 15 minutes at 4° C. The supernatant is used to prepare a 10-fold serial dilution in cell culture medium and viral titer is determined by a plaque assay as described.

Finally, the cell culture medium containing the swabs is vortexed briefly, centrifuged as described for fecal samples, and the supernatant is used for plaque assays directly. An aliquot of all undiluted samples is saved at −70° C. for future use.

Genetic stability of the chimeric BVDV in vivo can also be determined. Like the majority of RNA viruses, if not all, BVDV replication generates progenies with an average rate of mutation comparable to that of picornaviruses or influenza viruses ($10^{-4}$). The viruses used in our studies will have been previously selected to have reversion rates of $<10^{-6}$. It will be of great interest to determine if the viruses that were deemed stable by assessing reversion frequency in vitro display similar genetic stability in vivo. To obtain this information, the growth phenotype of representative virus recovered from animals at early and late stage of infection is evaluated. For each virus, four representative plaques from each of the samples collected the first day when virus was isolated from the animal are selected; four additional plaque from the same animals and tissues on the last date in which virus can be identified in the animals are also obtained. Small virus stocks will be produced from each plaque and subsequently titrated to establish its infectivity. Each animal-derived-virus stock is used to inoculate monolayers of bovine turbinate cells (ATCC CRL1390) at an input multiplicity of infection of 1 and progeny virus harvested at 12 and 16 hours after the infection.

All animal-derived-virus growth assays include a side-by-side control consisting of the parent virus derived from the infectious clone which was used to construct the chimeric clone. The harvested fluids will be titrated on bovine cell monolayers by a plaque assay. Growth comparison of inoculum vs. recovered virus will reveal if the original phenotype of the chimeric virus is maintained in animals at early and late times in the course of infection. Wild-type viruses will likely not arise in the inoculated animals, because the chimeric virus genome contains a deletion of the entire Npro gene. Regeneration of Npro can only results from a contaminating "helper virus". However, deletion of HCV protease gene may occur, especially when the chimeric virus has significant growth impairment in vivo. In any case, the resulting HCV protease-minus-virus may be of significant interest. The genetic changes underlying the restoration of the enhanced growth ability in the "revertant" virus will be determined by nucleotide sequence analysis. RT-PCR amplification of the chimeric region will be performed.

Although chimeric mutants are generally more stable than base substitutions, in some cases revertants or deletions arise at unexpectedly high frequency. The phenotypic reversion rates in vitro are determined before proceeding with animal studies.

In a preferred embodiment a virus with tropism for laboratory animals is employed. This will permit large scale testing for dose response under various conditions, toxicology, and pharmacokinetics, since groups of these animals are readily available and easy to work with.

EXAMPLES

The present invention will be better understood by reference to the following Examples, which are provided by way of exemplification and not by way of limitation.

Example 1
Construction and Testing of an HCV NS3-BVDV C Fusion

Materials and Methods

Cells, oligonucleotides and plasmids. Bacterial strain, JM109 (DE3) and XL-1Blue cells was purchased from Promega (Madison, Wis.) and Stratagene (La Jolla, Calif.), respectively. DNA oligonucleotides were purchased from Life Technologies (Gaithersburg, Md.) while RNA oligonucleotides were purchased from Oligo's Etc. Inc. (Wilsonville, Oreg.). Expression vector, pET-28a, was purchased from Novagen Inc. (Madison, Wis.). The full-length molecular clone (pVVNADL) of the cytopathic BVDV of NADL strain was described [Vassilev et al., J. Virol. 71:471–478 (1997)].

Construction of Functional NS4A tethered HCV NS3 protease. A single-chain recombinant cDNA plasmid of HCV NS3 protease (H strain), in which NS4A residues 21–32 (GSVVIVGRIVLS) (SEQ ID NO:2) was fused in frame to the amino terminus of the protease domain (residues 3–181) through a tetrapeptide linker (GSGS) (SEQ ID NO:4), was described previously [Taremi et al., Protein Sci. 7:2143–2149]. The mutation at amino acid residue 139 (from serine to alanine) was generated by using the 'Quick-Change' mutagenesis kit (Stratagene). The mutation in HCV NS3 protease was verified by dideoxynucleotide sequencing, using an Automated Sequencer (ABI377) from Perkin Elmer (Foster City, Calif.).

Construction of NS3-C fusion plasmid. cDNAs encoding NS4A tethered HCV NS3 protease and core of the cytopathic BVDV NADL strain (pVVNADL) was generated by using a standard polymerase chain reaction (PCR) method. A 5' PCR primer (V1F) coding for: (1) a NdeI site and (2) residues 21–25 of NS4A was designed as the forward primer; a 3' PCR primer (V1R) V1R) covering: (1) amino acid residues 175–181 of NS3 and (2) a BamHI site was engineered as the reverse primer. The resulting PCR amplified DNA fragment consists of the NS4A tethered HCV NS3 protease sandwiched by NdeI and BamHI sites. The BVDV core gene was amplified similarly by using a 5' primer (V2F) coding for: (1) a BamHI site, (2) the NS5A-5B junction site (GADTEDVVCC-SMSY) (SEQ ID NO:3) and (3) residues 1–7 of the core and a 3' primer (V2R) covering: (1) residues 97–102 of the core and (2) a EcoRI site. The resulting two PCR fragments were digested with the appropriate restriction enzymes and cloned in a three-way ligation in between the NdeI and EcoRI sites of pET-28a vector. The sequences of all clones were confirmed by dideoxynucleotide sequencing.

In vitro translation of HCV NS3 protease-BVDV core fusion protein. The wild type (HCV NS3wt-BVDV) and mutant (H4CV NS3mt-BVDV core) fusion proteins were expressed by using an in vitro transcription and translation system (Promega) and labeled with 35S-methionine (Amersham-Pharmacia Biotech, Arlington Heights, Ill.). The transcription-translation reaction products were analysed by 10–20% polyacrylamide gradient gel. The gel was dried prior to autoradiography.

Results

The present invention takes advantage of feature of BVDV Npro (that it is not an essential protein for viral growth), and also the availability of an infectious molecular clone of BVDV [Vassilev, et al., J. Virol. 71:471–478 (1997)]. The coding region of Npro was replaced by a gene coding for the NS4A cofactor-tethered HCV NS3 protease domain [Taremi, et al., Protein Sci. 7:2143–2149 (1998)]. This tethered HCV NS3 catalytic domain was then linked in-frame to the capsid (C) of BVDV through an HCV NS5A/5B junction site (FIGS. 1A and FIG. 2). In the resulting chimeric BVDV, the proteolytic function of BVDV Npro, which is responsible for cleaving the junction between Npro and C, was thus replaced by that of HCV NS3 protease. As shown in FIG. 2, the active NS4A-tethered HCV NS3 protease (NS3-wt) was responsible for cleaving the NS5A/NS5B junction, releasing the BVDV capsid from fusion with the HCV NS3 protease domain. There are four additional amino acids (from the N-terminus of HCV NS5B) that remain attached to the N-terminus of the capsid, which were expected and indeed found to be tolerated by BVDV.

As a control, we have also built another chimeric construct with an inactive tethered HCVNS3 (NS3-mt, with a mutation at amino acid 139 from Serine to Alanine). The lack of HCV NS3 protease activity resulted in non-cleavable HCV NS3-BVDV capsid fusion protein (BVDV/HCV-NS3-mt, FIG. 1C), thus rendering the capsid non-functional for encapsidation of the chimeric viral genome.

Figure 3:
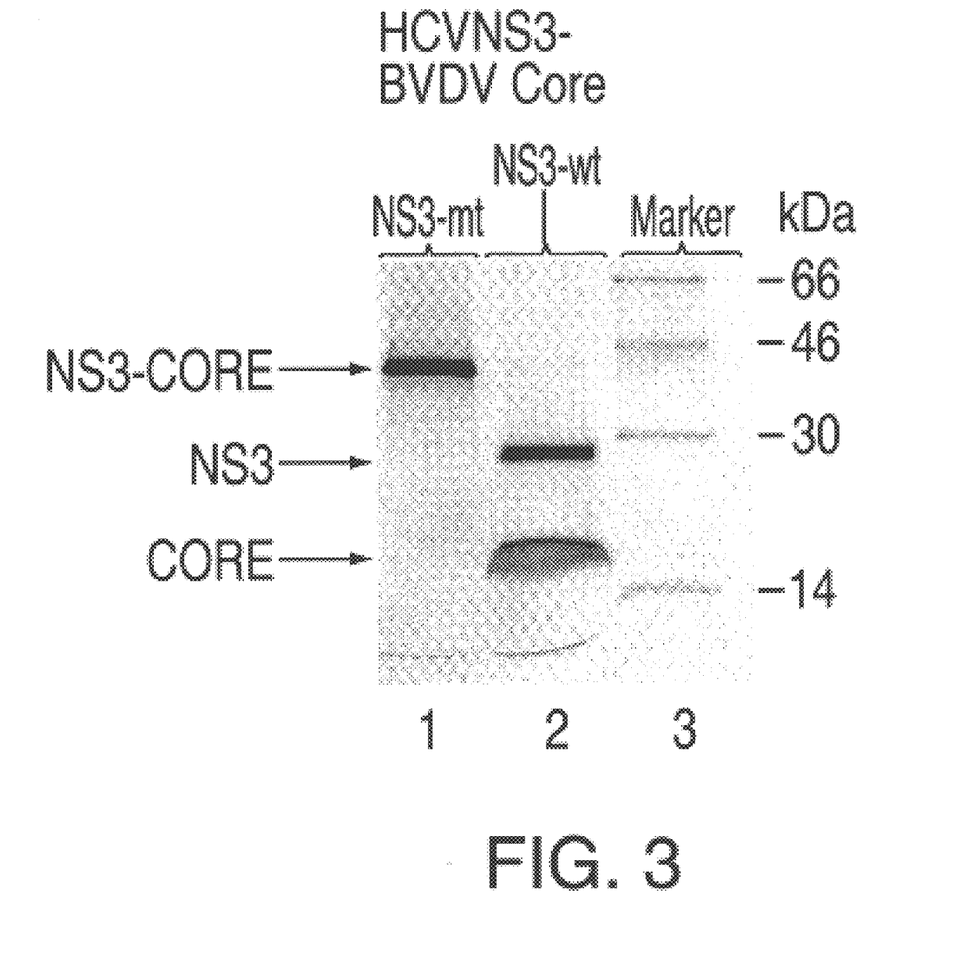
FIG. 3. Expression of HCV NS3-BVDV Core fusion polypeptide using an in vitro transcription and translation system labeled with $^{35}$S-methionine. A non-functional NS3-Core fusion protein (lane 1) and a functional HCV NS3-Core fusion protein (lane 2), in which the NS3 cleaves the polypeptide at the NS5A/NS5B junction into separate NS3 and Core proteins, were visualized by autoradiography of an SDS-PAGE gel. Lane 3 contains a marker proteins.

To demonstrate whether our chimeric constructs produced viral proteins as predicted, the NS4A-tethered HCV NS3-BVDV capsid (C) fusion proteins were expressed by using an in vitro transcription and translation system. The cleavage products as well as the NS3-C fusion precursors were labeled by $^{35}$S-labeled methionine and analyzed on an SDS-PAGE gel. As shown in FIG. 3, the active HCV NS3 protease (NS3-wt) generates the predicted cleavage products (HCV NS3 and BVDV core) very rapidly via a cis-cleavage; whereas the mutant HCV NS3 (NS3-mt) remains as the precursor, NS3-core fusion protein.

Example 2
Production of Infectious Chimeric Virus

Materials and Methods

Cell culture and virus stock. Madin-Darby bovine kidney (MDBK) cells were obtained from the American Type Culture Collection (CCL-22). MDBK cells were propagated in Eagle's modified minimal essential medium (EMEM) supplemented with 2 mM L-glutamine, 0.1 mM non-essential amino acids, 1.0 mM sodium pyruvate, 1.5 g/l sodium biocarbonate (Bio-Whitaker) and 10% heat inactivated horse serum (HS) from Sigma. Cells were maintained at 37° C. with 5% $CO_2$. The NADL strain of BVDV was derived from a molecular clone kindly provided by Dr. R O Donis [Vassilev et al., J. Virol. 71:471–478 (1997)] and amplified in MDBK cells.

Construction of recombinant BVDV/HCV NS3 plasmid. The chimeric clone (BVDV/HCV NS3-wt; SEQ ID NO: 1)

was constructed by PCR amplifications of the following three cDNA fragments: (1) T7 promoter sequence to the 7$^{th}$ codon of BVDV Npro (457 bp in size); (2) NS4A tethered HCV NS3-BVDV core fusion protein (938 bp in size from the HCV NS3-BVDV core expression plasmid) and (3) the first residue of BVDV Erns to the residue 347 of E2 (2334 bp in size). They were ligated together by using TaqPlus long PCR system. The resultant PCR fragment (3729 bp in size) was purified by on a preparative agarose gel, digested with ClaI and RsrII and cloned in the BVDV pVVNADL plamsid between ClaI and RsrII. The BVDV/HCV NS3-mut chimeric plasmid was generated by using a similar strategy.

In vitro transcription. The chimeric BVDV/HCV NS3 plasmid was used as the template for PCR amplification,to generate the linearized cDNA of the whole genome of BVDV/HCV NS3 together with T7 promoter. The PCR fragment (12.7 kb in size) was extracted with phenol/chloroform, and precipitated with ethanol. Two microgram of linearized DNA was transcribed in 20 μl, using the T7-MEGAscript kit from Ambion (Austin, Tex.). Reaction mixtures were incubated at 37° C. for 4 hrs in the absence of the cap analog. After transcription, the template DNA was degraded by DNaseI (2U per 20 μl reaction, 37° C. for 20 min). The transcribed RNAs were extracted and precipitated as described above. The full-length RNA transcripts were checked by agarose gel electrophoresis and stored at –80° C.

Transfection of MDBK cells. The transcribed RNAs were transfected in MDBK cells by electroporation as described [Mendez et al., J. Virol. 72:4737–4745 (1998)]. Briefly, MDBK cells (80% confluent) were trypsinized, washed three times with ice-cold PBS and resuspended at 2×10$^7$ cells/ml in ice-cold PBS. Five micrograms of transcribed RNAs were mixed with 0.1 ml of the cell suspension and pulsed with a Gene Pulser instrument (0.4 kV, 25 μF, infinite resistance, 2 pulses) from Bio-Rad (Hercules, Calif.). The electroporated mixture was mixed with 1 ml of EMEM and was plated on 75 cm$^2$ tissue culture flask. Transfected MDBK cells were incubated at 37° C. When the cytopathic effect was clearly observed, media containing progeny viruses were collected between 2–4 days of post-tansfection and used as an inoculum to infect MDBK cells. Mutant RNA transcripts of BVDV/HCV NS3-mut was produced and transfected into MDBK cells by the same strategy as described for the BVDV/HCV NS3-wt.

Virus infection. The BVDV/HCV NS3-wt chimeric viruses produced by the transfection of MDBK cells with chimeric RNA transcripts were used to infect MDBK cells (10$^6$, plated in 75cm$^2$ tissue culture flask). After one hour incubation at 37° C., 20 ml of EMEM with 10% HS was added and cells were incubated at 37° C. for 1 day. The medium containing the inoculum was removed and replaced with fresh medium. Cells were incubated at 37° C. for 24 days, or until cytopathic effect was observed. Medium containing progeny viruses (passage 1) was used as an inoculum for the plaque assay.

Plaque assay. The plaque assay was described previously by Mendez et al. [Mendez et al., J. Virol. 72:4737–4745 (1998)]. The BVDV/HCV NS3-wt chimeric viruses were serially diluted in EMEM. MDBK cells (0.5×10$^6$, plated in each well of 6-wells tissue culture plate) were infected at 37° C. with 0.5 ml of each dilution. Following an hour of adsorption, the inocula were removed. The cell monolayer was over-laid with 1% low-melting-point agarose in EMEM containing 10% HS. Plates were incubated for 3 days at 37° C. Four well-separated plaques of the chimeric virus were carefully removed and viruses in the agarose plugs were recovered in PBS for 2 hrs at room temperature. The recovered viruses from each plaque were used to infect MDBK cells for further amplification. To determine the chimeric virus titers, the agarose plugs were removed from the wells of the tissue culture plate. The monolayers of MDBK cells were fixed and stained with crystal violet staining solution containing 2.5% formaldehyde and 25% ethanol [Rice et al., New Biol. 1:285–296 (1989)].

Purification of chimeric viruses. Culture medium (20 ml) containing the progeny viruses of plaque-purified chimeric viruses (BVDV/HCV NS3-wt) was undergone a low-speed centrifugation (10,000 rpm for 10 mins at 40° C.). The medium was then loaded on a 10 ml cushion (30% sucrose in PBS) and centrifuged in the Beckman SW28 rotor for 10 hrs at 25,000 rpm at 4° C. The pellet of viruses was resuspended in PBS and was treated with RnaseA(0.5 mg/ml) from Borhering (Indianapolis, Ind.) and RQ1-DNaseI(1 U/ml) from Promega for 3 hrs at 37° C. before the isolation of viral RNAs.

Isolation of viral RNA and amplification of cDNA by RT-PCR. RNAs from infected cells or from PBS suspension after ultra-centrifugation was obtained by using RNeasy mini kit from Qiagen (Valencia, Calif.), according to the manufacturer's protocol. RT-PCR was preformed on the RNA samples by using Thermoscript™ RT-PCR system from Life technologies and synthetic oligonucleotides (V1F, corresponding to the 5' end of the NS4A tethered HCV NS3 and V2F, corresponding to the 3' end of the BVDV capsid as described previously). RNA samples of chimeric viruses without the addition of reversed transcriptase or RNA from the wild type BVDV were used as negative controls of the RT-PCR.

Western blotting analysis. SDS-solubilized lysates obtained from infected MDBK cells, were separated by SDS-PAGE (10–20%) and electrotransferred onto a nitrocellular membrane as described previously [Hong et al., J. Virol. 70:4261–4268 (1996)]. The polyclonal antibody against the HCV NS3 and monoclonal antibody against the BVDV NS3 were used as the primary antibodies and the alkaline phosphate-conjugated anti-mouse IgG and anti-rabbit IgG antibodies (Promega) as the secondary antibodies.

Results

Two chimeric clones, BVDV/HCV NS3-wt (SEQ ID NO:1) and BVDV/HCV NS3-mt ("wt" indicates a wild-type NS3 protease domain, "mt" indicates a mutated NS3 protease domain), were constructed as illustrated in FIG. 1. The full-length RNA transcripts were produced by T7 polymerase in an in vitro transcription reaction as described [Vassilev, supra]. The RNA transcripts were transfected into MDBK cells by the electroporation method [Xu, et. al., J. Virol. 71:5312–5322 (1997); Mendez, et al., J. Virol. 72:4737–4745 (1998)]. Production of any viable viruses was examined microscopically for virally-induced cytopathic effect. Our results showed that the RNA transcript from the chimeric BVDV/HCV NS3-wt clone generated cytopathic viruses, whereas the mutant clone (BVDV/HCV NS3-mt) failed to produced any signs of infection. In a plaque assay, the chimeric virus was quantified and the size of the plaque appeared to be smaller than the wild type BVDV (isolate NADL).

Figure 4A:
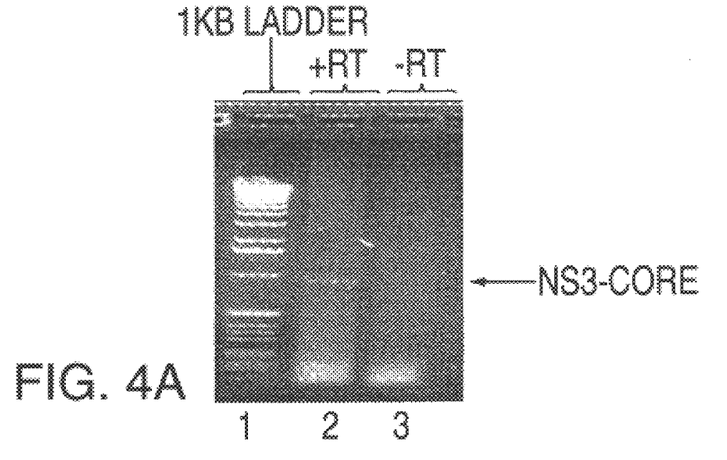
FIGS. 4A, 4B, and 4C. (A) RT-PCR analysis for viral RNA (and the absence of DNA) encoding the HCV NS3-BVDV C fusion. The NS3-Core fragment was amplified in the presence (lane 2) but not in the absence (lane 3) of reverse transcriptase. Lane 1 contains a 1 kb ladder. (B) Western blot analysis of the expression of NS4A tethered HCV NS3 from chimeric virus. Lane 1: MDBK lysate (negative control); Lane 2: molecular weight markers; Lanes 3 and 4: two different plaque purified viruses; Lane 5: BVDV (negative control). (C) Western blot analysis for the production of BVDV proteins NS2-NS3 and NS3 from chimeric virus. Lanes 1 and 2: two different plaque purified viruses; Lane 3: MDBK.

After serial passages, plaques from the chimeric virus were isolated and amplified. The viruses in the supernatant were purified by ultracentrifugation over a sucrose-gradient and viral RNAs were isolated. Fresh MDBK cells were infected with the plaque-purified chimeric virus. Reverse transcription and polymerase chain reaction (RT-PCR) were performed with an HCV NS3 specific forward primer and a BVDV capsid-specific reverse primer. As shown in FIG. 4A, a predicted HCV NS3-BVDV C fragment was amplified (lane 2), suggesting that the viruses in the supernatant are the chimeric BVDV. As a control, PCR alone (without RT, or −RT) fails to amplify the fusion fragment (lane 3), confirming that the DNA fragment is derived from viral RNA, not from a contaminating DNA sources. The fusion fragment from RT-PCR was then cloned and sequenced, the results further confirmed the identity of its origin from the chimeric clone (data not shown).

Figure 4B:
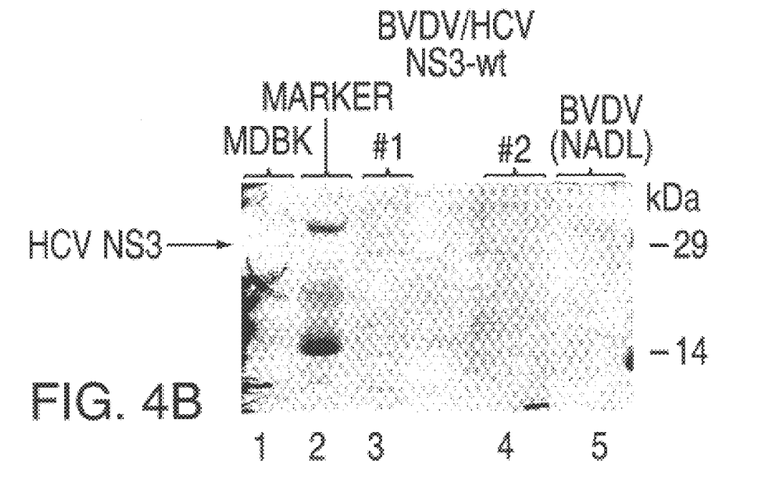
Figure 4C:
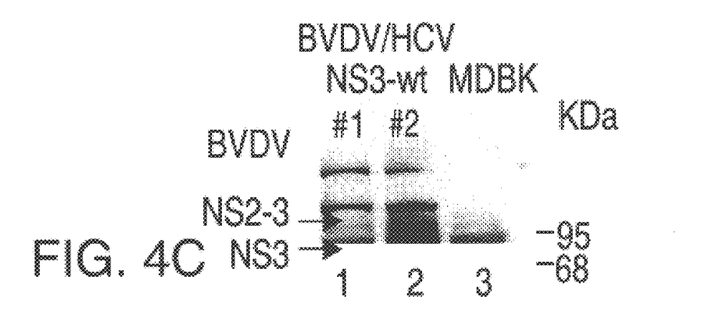

The infected cell lysates were also analyzed by western blotting. As shown in FIG. 4B, both plaque purified viruses (#1 and #2) produced HCV NS3 protease in the cells corresponding to the size of the tethered protease domain (lanes 3 and 4). In addition, the chimeric viruses generated both BVDV NS2-3 and NS3 proteins as determined by western blotting analysis traced with the anti-BVDV NS3 antibodies FIG. 4C, lanes 1 and 2). The presence of abundant BVDV NS3 compared to NS2-3 explained why the chimeric viruses were cytopathic [Meyers, and Thiel, Virus Res. 47:53–118 (1996)]. The cytopathic property of the chimeric viruses allows convenient quantification of viral titers through a plague assay or an infectivity assay.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, are approximate, and are provided for description.

All patents, patent applications, publications, and other materials cited herein are hereby incorporated herein reference in their entireties.

What is claimed is:

1. A nucleic acid construct encoding a chimeric Hepatitis C Virus (HCV)-pestivirus genome, which nucleic acid construct comprises a pestivirus genome wherein (i) a Npro pestivirus protease gene is replaced with a gene encoding a functional HCV NS3 protease, and (ii) each junction site recognized by the Npro pestivirus protease is replaced with a junction site recognized by the HCV NS3 protease.

2. The nucleic acid construct of claim 1, wherein the functional HCV NS3 protease is encoded by a gene comprising a sequence coding for an HCV NS4A cofactor tethered to the N-terminus of the HCV NS3 protease domain.

3. The nucleic acid construct of claim 1, wherein the pestivirus is a Bovine Viral Diarrhea Virus (BVDV).

4. The nucleic acid construct of claim 1, wherein the junction site recognized by the HCV NS3 protease is linked to a gene encoding a BVDV capsid protein, whereby the HCV NS3 protease cleaves the junction between itself and the capsid protein.

5. The nucleic acid construct of claim 1, wherein the junction site recognized by the HCV NS3 protease is an HCV NS5A/NS5B junction site.

6. The nucleic acid construct of claim 3, wherein the chimeric genome has a genome structure as depicted in FIG. 2.

7. The nucleic acid construct of claim 1 which is a DNA.

8. The nucleic acid construct of claim 1 which is an infectious RNA.

9. A cell transfected with the infectious RNA of claim 8.

10. The cell of claim 9 which is of bovine origin.

11. A method for propagating an infectious, plaque-forming chimeric HCV-pestivirus, which method comprises culturing a cell of claim 9 under conditions that permit production of viable virus.

12. The method of claim 11, wherein production of viable virus is detected by observing a cytopathic effect in the cells.

13. The method of claim 11, wherein the pestivirus is BVDV.

14. A method of screening for a compound that inhibits an HCV protease, which method comprises evaluating viral infection of the cells of claim 9 cultured under conditions that permit production of viable viruses, wherein one set of cells are cultured in the presence of a candidate compound (test cells) and a different set of cells are cultured in the absence of the candidate compound (control cells), and wherein a reduction in viral infection in test relative to control cells indicates that the compound inhibits an HCV protease.

15. An infectious, plaque-forming chimeric HCV-pestivirus, which has a genome comprising a pestivirus genome wherein (i) a Npro pestivirus protease gene is replaced with a gene encoding a functional HCV NS3 protease, and (ii) each junction site recognized by the Npro pestivirus protease is replaced with a junction site recognized by the HCV NS3 protease.

16. The chimeric HCV-pestivirus of claim 15, wherein the functional HCV protease is encoded by a gene comprising a sequence coding for an HCV NS4A cofactor tethered to the N-terminus of the HCV NS3 protease domain.

17. The chimeric HCV-pestivirus of claim 15, wherein the junction site recognized by the HCV NS3 protease is an HCV NS5A/NS5B junction site.

18. The chimeric HCV-pestivirus of claim 15, wherein the pestivirus is BVDV.

19. The chimeric HCV-pestivirus of claim 15, wherein the junction site recognized by the HCV NS3 protease is linked to a gene encoding a BVDV capsid protein, whereby the HCV NS3 protease cleaves the junction between itself and the capsid protein.

20. The chimeric HCV-pestivirus of claim 18, wherein the chimeric genome has a genome structure as depicted in FIG. 2.

* * * * *

SEQUENCE LISTING

<160> NUMBER OF SEQ ID NOS: 4

<210> SEQ ID NO 1
<211> LENGTH: 12734
<212> TYPE: DNA
<213> ORGANISM: Artificial Sequence
<220> FEATURE:
<223> OTHER INFORMATION: Description of Artificial Sequence: Chimeric Pestivirus

<400> SEQUENCE: 1

```
gtatacgaga attagaaaag gcactcgtat acgtattggg caattaaaaa taataattag      60
gcctagggaa caaatccctc tcagcgaagg ccgaaaagag gctagccatg cccttagtag     120
gactagcata atgaggggggg tagcaacagt ggtgagttcg ttggatggct taagccctga     180
gtacagggta gtcgtcagtg gttcgacgcc ttggaataaa ggtctcgaga tgccacgtgg     240
acgagggcat gcccaaagca catcttaacc tgagcggggg tcgcccaggt aaaagcagtt     300
ttaaccgact gttacgaata cagcctgata gggtgctgca gaggcccact gtattgctac     360
taaaaatctc tgctgtacat ggcacatgga gttgatcaca aatgaaggat ccggtagtgt     420
tgttattgtt ggtagaattg ttttatctgg tagtggtagt atcacggcgt acgcccagca     480
gacgagaggc ctcctagggt gtaagatcac cagtctgact ggccgggaca aaaaccaagt     540
ggagggtgag gtccagatcg tgtcaactgc tacccaaacc ttcctggcaa cgtgcatcaa     600
tggggtatgc tggactgtct accacggggc cggaacgagg accatcgcat cacccaaggg     660
tcctgtcatc cagatgtata ccaatgtgga ccaagacctt gtgggctggc ccgctcctca     720
aggttcccgc tcattgacac cctgcacctg cggctcctcg gaccttttacc tggttacgag     780 gcacgccgac gtcattcccg tgcgccggcg aggtgatagc aggggtagcc tgctttcgcc     840
ccggcccatt tcctacctaa aaggctcctc gggggggtccg ctgttgtgcc ccgcgggaca     900
cgccgtgggc ctattcaggg ccgcggtgtg cacccgtgga gtggccaagg cggtggactt     960
tatccctgtg gagaacctag agacaaccat gagatccgga tccggtgcag acactgaaga    1020
tgtcgtgtgt tgctcaatgt cctattcaga cacgaaagaa gagggagcaa caaaaaagaa    1080
aacacagaaa cccgacagac tagaaagggg gaaaatgaaa atagtgccca aagaatctga    1140
aaaagacagc aaaactaaac ctccggatgc tacaatagtg gtggaaggag tcaaatacca    1200
```

```
ggtgaggaag aagggaaaaa ccaagagtaa aaacactcag gacggcttgt accataacaa    1260
aaacaaacct caggaatcac gcaagaaact ggaaaaagca ttgttggcgt gggcaataat    1320
agctatagtt ttgtttcaag ttacaatggg agaaaacata acacagtgga acctacaaga    1380
taatgggacg aagggatac aacgggcaat gttccaaagg ggtgtgaata gaagtttaca    1440
tggaatctgg ccagagaaaa tctgtactgg cgtcccttcc catctagcca ccgatataga    1500
actaaaaaca attcatggta tgatggatgc aagtgagaag accaactaca cgtgttgcag    1560
acttcaacgc catgagtgga acaagcatgg ttggtgcaac tggtacaata ttgaaccctg    1620
gattctagtc atgaatagaa cccaagccaa tctcactgag ggacaaccac caagggagtg    1680
cgcagtcact tgtaggtatg ataggggctag tgacttaaac gtggtaacac aagctagaga    1740
tagccccaca cccttaacag gttgcaagaa aggaaagaac ttctcctttg caggcatatt    1800
gatgcggggc ccctgcaact ttgaaatagc tgcaagtgat gtattattca agaacatga     1860 acgcattagt atgttccagg atactactct ttaccttgtt gacgggttga ccaactcctt    1920
agaaggtgcc agacaaggaa ccgctaaact gacaacctgg ttaggcaagc agctcgggat    1980
actaggaaaa aagttggaaa acaagagtaa gacgtggttt ggagcatacg ctgcttcccc    2040
ttactgtgat gtcgatcgca aaattggcta catatggtat acaaaaaatt gcacccctgc    2100
ctgcttaccc aagaacacaa aaattgtcgg ccctgggaaa tttgacacca atgcagagga    2160
cggcaagata ttcatgagaa tggggggtca cttgtcggag gtactactac tttctttagt    2220
ggtgctgtcc gacttcgcac cggaaacagc tagtgtaatg tacctaatcc tacatttttc    2280
catcccacaa agtcacgttg atgtaatgga ttgtgataag acccagttga acctcacagt    2340
ggagctgaca acagctgaag taataccagg gtcggtctgg aatctaggca aatatgtatg    2400
tataagacca aattggtggc cttatgagac aactgtagtg ttggcatttg aagaggtgag    2460
ccaggtggtg aagttagtgt tgagggcact cagagattta acacgcattt ggaacgctgc    2520
aacaactact gctttttttag tatgccttgt taagatagtc aggggccaga tggtacaggg    2580
cattctgtgg ctactattga taacagggggt acaagggcac ttggattgca aacctgaatt    2640
ctcgtatgcc atagcaaagg acgaaagaat tggtcaactg ggggctgaag gccttaccac    2700
cacttggaag gaatactcac ctggaatgaa gctggaagac acaatggtca ttgcttggtg    2760
cgaagatggg aagttaatgt acctccaaag atgcacgaga gaaaccagat atctcgcaat    2820
cttgcataca agagccttgc cgaccagtgt ggtattcaaa aaactctttg atgggcgaaa    2880
gcaagaggat gtagtcgaaa tgaacgacaa cttttgaattt ggactctgcc catgtgatgc    2940
caaacccata gtaagaggga agttcaatac aacgctgctg aacggaccgg ccttccagat    3000
ggtatgcccc ataggatgga cagggactgt aagctgtacg tcattcaata tggacacctt    3060
agccacaact gtggtacgga catatagaag gtctaaacca ttccctcata ggcaaggctg    3120
tatcacccaa aagaatctgg gggaggatct ccataactgc atccttggag gaaattggac    3180
ttgtgtgcct ggagaccaac tactatacaa aggggctct attgaatctt gcaagtggtg    3240
tggctatcaa tttaaagaga gtgagggact accacactac cccattggca agtgtaaatt    3300
ggagaacgag actggttaca ggctagtaga cagtacctct tgcaatagag aaggtgtggc    3360
catagtacca caagggacat taaagtgcaa gataggaaaa acaactgtac aggtcatagc    3420 tatggataccc aaactcggac ctatgccttg cagaccatat gaaatcatat caagtgaggg    3480
gcctgtagaa aagacagcgt gtactttcaa ctacactaag acattaaaaa ataagtattt    3540
```

-continued

```
tgagcccaga gacagctact ttcagcaata catgctaaaa ggagagtatc aatactggtt    3600
tgacctggag gtgactgacc atcaccggga ttacttcgct gagtccatat tagtggtggt    3660
agtagccctc ttgggtggca gatatgtact ttggttactg gttacataca tggtcttatc    3720
agaacagaag gccttaggga ttcagtatgg atcagtggaa gtggtgatga tgggcaactt    3780
gctaacccat aacaatattg aagtggtgac atacttcttg ctgctgtacc tactgctgag    3840
ggaggagagc gtaaagaagt gggtcttact cttataccac atcttagtgg tacacccaat    3900
caaatctgta attgtgatcc tactgatgat tgggatgtg gtaaaggccg attcaggggg     3960
ccaagagtac ttggggaaaa tagacctctg ttttacaaca gtagtactaa tcgtcatagg    4020
tttaatcata gccaggcgtg acccaactat agtgccactg gtaacaataa tggcagcact    4080
gagggtcact gaactgaccc accagcctgg agttgacatc gctgtggcgg tcatgactat    4140
aaccctactg atggttagct atgtgacaga ttattttaga tataaaaaat ggttacagtg    4200
cattctcagc ctggtatctg gggtgttctt gataagaagc ctaatatacc taggtagaat    4260
cgagatgcca gaggtaacta tcccaaactg gagaccacta actttaatac tattatattt    4320
gatctcaaca acaattgtaa cgaggtggaa ggttgacgtg gctggcctat tgttgcaatg    4380
tgtgcctatc ttattgctgg tcacaacctt gtgggccgac ttcttaaccc taatactgat    4440
cctgcctacc tatgaattgg ttaaattata ctatctgaaa actgttagga ctgatataga    4500
aagaagttgg ctaggggga tagactatac aagagttgac tccatctacg acgttgatga    4560
gagtggagag ggcgtatatc tttttccatc aaggcagaaa gcacagggga attttctat    4620
actcttgccc cttatcaaag caacactgat aagttgcgtc agcagtaaat ggcagctaat    4680
atacatgagt tacttaactt tggactttat gtactacatg cacaggaaag ttatagaaga    4740
gatctcagga ggtaccaaca taatatccag gttagtggca gcactcatag agctgaactg    4800
gtccatggaa gaagaggaga gcaaaggctt aaagaagttt tatctattgt ctggaaggtt    4860
gagaaaccta ataataaaac ataaggtaag gaatgagacc gtggcttctt ggtacgggga    4920
ggaggaagtc tacggtatgc caaagatcat gactataatc aaggccagta cactgagtaa    4980
gagcaggcac tgcataatat gcactgtatg tgagggccga gagtggaaag gtggcacctg    5040
cccaaaatgt ggacgccatg ggaagccgat aacgtgtggg atgtcgctag cagatttcga    5100
agaaagacac tataaaagaa tctttataag ggaaggcaac tttgagggta tgtgcagccg    5160
atgccaggga aagcatagga ggtttgaaat ggaccgggaa cctaagagtg ccagatactg    5220
tgctgagtgt aataggctgc atcctgctga ggaaggtgac ttttgggcag agtcgagcat    5280
gttgggcctc aaaatcacct actttgcgct gatggatgga aaggtgtatg atatcacaga    5340
gtgggctgga tgccagcgtg tgggaatctc cccagatacc cacagagtcc cttgtcacat    5400
ctcatttggt tcacggatgc ctttcaggca ggaatacaat ggctttgtac aatataccgc    5460
tagggggcaa ctatttctga gaaacttgcc cgtactggca actaaagtaa aaatgctcat    5520
ggtaggcaac cttggagaag aaattggtaa tctggaacat cttgggtgga tcctaagggg    5580
gcctgccgtg tgtaagaaga tcacagagca cgaaaaatgc cacattaata tactggataa    5640
actaaccgca ttttcggga tcatgccaag ggggactaca cccagagccc cggtgaggtt    5700
ccctacgagc ttactaaaag tgaggagggg tctggagact ggctgggctt acacacacca    5760
aggcgggata agttcagtcg accatgtaac cgccggaaaa gatctactgg tctgtgacag    5820
catgggacga actagagtgg tttgccaaag caacaacagg ttgaccgatg agacagtata    5880
tggcgtcaag actgactcag ggtgcccaga cggtgccaga tgttatgtgt taaatccaga    5940
```

-continued

```
ggccgttaac atatcaggat ccaaaggggc agtcgttcac ctccaaaaga caggtggaga     6000
attcacgtgt gtcaccgcat caggcacacc ggctttcttc gacctaaaaa acttgaaagg     6060
atggtcaggc ttgcctatat ttgaagcctc cagcgggagg gtggttggca gagtcaaagt     6120
agggaagaat gaagagtcta aacctacaaa ataatgagt ggaatccaga ccgtctcaaa      6180
aaacacagca gacctgaccg agatggtcaa gaagataacc agcatgaaca ggggagactt     6240
caagcagatt actttggcaa caggggcagg caaaaccaca gaactcccaa agcagttat      6300 agaggagata ggaagacaca agagagtatt agttcttata ccattaaggg cagcggcaga     6360
gtcagtctac cagtatatga gattgaaaca cccaagcatc tcttttaacc taaggatagg     6420
ggacatgaaa gaggggggaca tggcaaccgg gataacctat gcatcatacg ggtacttctg    6480
ccaaatgcct caaccaaagc tcagagctgc tatggtagaa tactcataca tattcttaga    6540
tgaataccat tgtgccactc ctgaacaact ggcaattatc gggaagatcc acagattttc    6600
agagagtata agggttgtcg ccatgactgc cacgccagca gggtcggtga ccacaacagg    6660
tcaaaagcac ccaatagagg aattcatagc ccccgaggta atgaaagggg aggatcttgg    6720
tagtcagttc cttgatatag cagggttaaa ataccagtg gatgagatga aggcaatat     6780 gttggttttt gtaccaacga gaaacatggc agtagaggta gcaagaagc taaaagctaa    6840 gggctataac tctggatact attacagtgg agaggatcca gccaatctga gagttgtgac    6900
atcacaatcc ccctatgtaa tcgtggctac aaatgctatt gaatcaggag tgacactacc    6960
agatttggac acggttatag acacggggtt gaaatgtgaa agagggtga gggtatcatc    7020 aaagataccc ttcatcgtaa caggccttaa gaggatggcc gtgactgtgg gtgagcaggc    7080
gcagcgtagg ggcagagtag gtagagtgaa acccggggagg tattatagga gccaggaaac   7140
agcaacaggg tcaaaggact accactatga cctcttgcag gcacaaagat acgggattga    7200
ggatggaatc aacgtgacga aatcctttag ggagatgaat tacgattgga gcctatacga    7260
ggaggacagc ctactaataa cccagctgga aatactaaat aatctactca tctcagaaga    7320
cttgccagcc gctgttaaga acataatggc caggactgat cacccagagc caatccaact    7380
tgcatacaac agctatgaag tccaggtccc ggtcctattc ccaaaaataa ggaatggaga    7440
agtcacagac acctacgaaa attactcgtt tctaaatgcc agaaagttag gggaggatgt    7500
gcccgtgtat atctacgcta ctgaagatga ggatctggca gttgacctct tagggctaga    7560
ctggcctgat cctgggaacc agcaggtagt ggagactggt aaagcactga agcaagtgac    7620
cgggttgtcc tcggctgaaa atgccctact agtggcttta tttgggtatg tgggttacca    7680
ggctctctca aagaggcatg tcccaatgat aacagacata tataccatcg aggaccagag    7740
actagaagac accacccacc tccagtatgc acccaacgcc ataaaaaccg atgggacaga    7800
gactgaactg aaagaactgg cgtcgggtga cgtggaaaaa atcatgggag ccatttcaga    7860
ttatgcagct ggggactgg agtttgttaa atcccaagca gaaaagataa aaacagctcc    7920
tttgtttaaa gaaacgcag aagccgcaaa agggtatgtc caaaaattca ttgactcatt    7980
aattgaaaat aaagaagaaa taatcagata tggtttgtgg ggaacacaca cagcactata   8040
caaaagcata gctgcaagac tggggcatga acagcgtttt gccacactag tgttaaagtg    8100
gctagctttt ggaggggaat cagtgtcaga ccacgtcaag caggcggcag ttgatttagt    8160
ggtctattat gtgatgaata agccttcctt cccaggtgac tccgagacac agcaagaagg    8220
gaggcgattc gtcgcaagcc tgttcatctc cgcactggca acctacacat acaaaacttg    8280
```

-continued

```
gaattaccac aatctctcta aagtggtgga accagccctg gcttacctcc cctatgctac    8340
cagcgcatta aaaatgttca ccccaacgcg gctggagagc gtggtgatac tgagcaccac    8400
gatatataaa acatacctct ctataaggaa ggggaagagt gatggattgc tgggtacggg    8460
gataagtgca gccatggaaa tcctgtcaca aaacccagta tcggtaggta tatctgtgat    8520
gttgggggta gggcaatcg ctgcgcacaa cgctattgag tccagtgaac agaaaaggac     8580
cctacttatg aaggtgtttg taaagaactt cttggatcag gctgcaacag atgagctggt    8640
aaagaaaaac ccagaaaaaa ttataatggc cttatttgaa gcagtccaga caattggtaa    8700
ccccctgaga ctaatatacc acctgtatgg ggtttactac aaaggttggg aggccaagga    8760
actatctgag aggacagcag gcagaaactt attcacattg ataatgtttg aagccttcga    8820
gttattaggg atggactcac aagggaaaat aaggaacctg tccggaaatt acattttgga    8880
tttgatatac ggcctacaca agcaaatcaa cagagggctg aagaaaatgg tactgggtg    8940
ggcccctgca cccttagtt gtgactggac ccctagtgac gagaggatca gattgccaac    9000
agacaactat ttgagggtag aaaccaggtg cccatgtggc tatgagatga aagctttcaa    9060
aaatgtaggt ggcaaactta ccaaagtgga ggagagcggg cctttcctat gtagaaacag    9120
acctggtagg ggaccagtca actacagagt caccaagtat tacgatgaca acctcagaga    9180
gataaaacca gtagcaaagt tggaaggaca ggtagagcac tactacaaag gggtcacagc    9240
aaaaattgac tacagtaaag gaaaaatgct cttggccact gacaagtggg aggtggaaca    9300
tggtgtcata accaggttag ctaagagata tactgggtc gggttcaatg gtgcatactt     9360
aggtgacgag cccaatcacc gtgctctagt ggagagggac tgtgcaacta taaccaaaaa    9420
cacagtacag tttctaaaaa tgaagaaggg gtgtgcgttc acctatgacc tgaccatctc    9480
caatctgacc aggctcatcg aactagtaca caggaacaat cttgaagaga aggaaatacc    9540
caccgctacg gtcaccacat ggctagctta caccttcgtg aatgaagacg tagggactat    9600
aaaaccagta ctaggagaga gagtaatccc cgaccctgta gttgatatca atttacaacc    9660
agaggtgcaa gtggacacgt cagaggttgg gatcacaata attggaaggg aaaccctgat    9720
gacaacggga gtgacacctg tcttggaaaa agtagagcct gacgccagcg acaaccaaaa    9780
ctcggtgaag atcgggttgg atgagggtaa ttacccaggg cctggaatac agacacatac    9840
actaacagaa gaaatacaca cagggatgc gaggcccttc atcatgatcc tgggctcaag    9900
gaattccata tcaaatag gg caaagactgc tagaaatata aatctgtaca caggaaatga    9960
ccccagggaa atacgagact tgatggctgc agggcgcatg ttagtagtag cactgaggga   10020
tgtcgaccct gagctgtctg aaatggtcga tttcaagggg actttttag ataggaggc     10080
cctggaggct ctaagtctcg ggcaacctaa accgaagcag gttaccaagg aagctgttag   10140
gaatttgata gaacagaaaa aagatgtgga gatccctaac tggtttgcat cagatgaccc   10200
agtatttctg gaagtggcct taaaaaatga taagtactac ttagtaggag atgttggaga   10260
gctaaaagat caagctaaag cacttgggc cacggatcag acaagaatta taaaggaggt    10320
aggctcaagg acgtatgcca tgaagctatc tagctggttc ctcaaggcat caaacaaaca   10380
gatgagttta actccactgt ttgaggaatt gttgctacgg tgcccacctg caactaagag   10440
caataagggg cacatggcat cagcttacca attggcacag ggtaactggg agccctcgg    10500
ttgcgggtg cacctaggta caataccagc cagaagggtg aagatacacc catatgaagc   10560
ttacctgaag ttgaaagatt tcatagaaga agaagagaag aaacctaggg ttaaggatac   10620
agtaataaga gagcacaaca aatggatact taaaaaaata aggtttcaag gaaaccctcaa  10680
```

```
caccaagaaa atgctcaacc cagggaaact atctgaacag ttggacaggg aggggcgcaa    10740
gaggaacatc tacaaccacc agattggtac tataatgtca agtgcaggca taaggctgga    10800
gaaattgcca atagtgaggg cccaaaccga caccaaaacc tttcatgagg caataagaga    10860
taagatagac aagagtgaaa accggcaaaa tccagaattg cacaacaaat tgttggagat    10920
tttccacacg atagcccaac ccaccctgaa acacacctac ggtgaggtga cgtgggagca    10980
acttgaggcg ggggtaaata gaaggggggc agcaggcttc ctggagaaga gaacatcgg     11040 agaagtattg gattcagaaa agcacctggt agaacaattg gtcagggatc tgaaggccgg    11100
gagaaagata aaatattatg aaactgcaat accaaaaaat gagaagagag atgtcagtga    11160
tgactggcag gcaggggacc tggtggttga agaggccca agagttatcc aatacccctga   11220 agccaagaca aggctagcca tcactaaggt catgtataac tgggtgaaac agcagcccgt    11280
tgtgattcca ggatatgaag gaagaccccc cttgttcaac atctttgata agtgagaaa    11340 ggaatgggac tcgttcaatg agccagtggc cgtaagtttt gacaccaaag cctgggacac    11400
tcaagtgact agtaaggatc tgcaacttat tggagaaatc cagaaatatt actataagaa    11460
ggagtggcac aagttcattg acaccatcac cgaccacatg acagaagtac cagttataac    11520
agcagatggt gaagtatata taagaaatgg gcagagaggg agcggccagc cagacacaag    11580
tgctggcaac agcatgttaa atgtcctgac aatgatgtac ggcttctgcg aaagcacagg    11640
ggtaccgtac aagagtttca caggggtggc aaggatccac gtctgtgggg atgatggctt    11700
cttaataact gaaaagggt tagggctgaa atttgctaac aaagggatgc agattcttca    11760
tgaagcaggc aaaccctcaga agataacgga agggaaaag atgaaagttg cctatagatt    11820
tgaggatata gagttctgtt ctcataccc agtccctgtt aggtggtccg acaacaccag    11880
tagtcacatg gccgggagag acaccgctgt gatactatca agatggcaa caagattgga    11940 ttcaagtgga gagaggggta ccacagcata tgaaaaagcg gtagccttca gtttcttgct    12000
gatgtattcc tggaacccgc ttgttaggag gatttgcctg ttggtccttt cgcaacagcc    12060
agagacagac ccatcaaaac atgccactta ttattacaaa ggtgatccaa taggggccta    12120
taaagatgta ataggtcgga atctaagtga actgaagaga acaggctttg agaaattggc    12180
aaatctaaac ctaagcctgt ccacgttggg ggtctggact aagcacacaa gcaaaagaat    12240
aattcaggac tgtgttgcca ttgggaaaga agagggcaac tggctagtta agcccgacag    12300
gctgatatcc agcaaaactg gccacttata catacctgat aaaggcttta cattacaagg    12360
aaagcattat gagcaactgc agctaagaac agagacaaac ccggtcatgg gggttgggac    12420
tgagagatac aagttaggtc ccatagtcaa tctgctgctg agaaggttga aaattctgct    12480
catgacggcc gtcggcgtca gcagctgaga caaaatgtat atattgtaaa taaattaatc    12540
catgtacata gtgtatataa atatagttgg gaccgtccac ctcaagaaga cgacacgccc    12600
aacacgcaca gctaaacagt agtcaagatt atctacctca agataacact acatttaatg    12660
cacacagcac tttagctgta tgaggatacg cccgacgtct atagttggac tagggaagac    12720
ctctaacagc cccc                                                      12734
```

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: NS4A residues 21-32

-continued

```
<400> SEQUENCE: 2

Gly Ser Val Val Ile Val Gly Arg Ile Val Leu Ser
  1               5                  10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: HCV
      NS5A/5B junction sequence

<400> SEQUENCE: 3

Gly Ala Asp Thr Glu Asp Val Val Cys Cys Ser Met Ser Tyr
  1               5                  10

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Linker

<400> SEQUENCE: 4

Gly Ser Gly Ser
```